United States Patent [19]

Martinez et al.

[11] Patent Number: 4,687,760

[45] Date of Patent: Aug. 18, 1987

[54] REDUCED PEPTIDES WHICH INHIBIT GASTRIC SECRETION, PROCESS FOR THEIR PREPARATION AND PHARMACEUTICAL COMPOSITIONS IN WHICH THEY ARE PRESENT

[75] Inventors: Jean Martinez, Caux; Jean-Pierre Bali, Saint-Gely Du Fesc; Richard Magous, Lunel; Bertrand Castro, Saint-Aunes; Henri Demarne, Montpellier, all of France

[73] Assignees: Sanofi; Centre National de la Recherche Scientifque (CNRS)

[21] Appl. No.: 809,131

[22] Filed: Dec. 16, 1985

[30] Foreign Application Priority Data

Dec. 20, 1984 [FR] France ............................ 84 19544

[51] Int. Cl.$^4$ .................... A61K 37/43; C07K 5/02; C07K 5/08; C07K 5/10
[52] U.S. Cl. ................................. 514/18; 530/332; 530/331; 530/330
[58] Field of Search ............... 530/330, 331, 332; 260/998.2; 514/18

[56] References Cited

FOREIGN PATENT DOCUMENTS 0012401 6/1980 European Pat. Off. ............ 530/330
2533210 12/1984 France .
1042481 9/1966 United Kingdom .

*Primary Examiner*—Delbert R. Phillips
*Attorney, Agent, or Firm*—Bacon & Thomas

[57] ABSTRACT

The invention relates to the peptides of the formula:

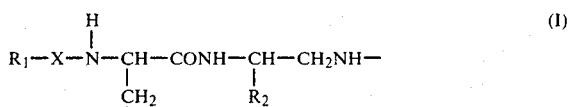
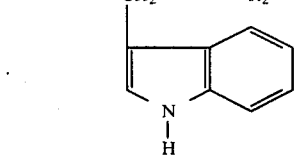

in which:

$R_1$ represents hydrogen or a protecting group for the amine group, such as t-butoxycarbonyl, benzyloxycarbonyl or lower alkanoyl groups;

X represents beta-alanine glycine or a direct bond between $R_1$ and the amine group; and $R_2$ represents a group chosen from:

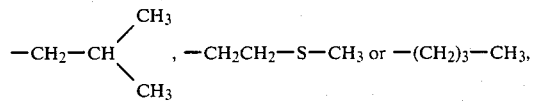

corresponding to the side chains of the natural amino acid leucine, methionine and norleucine.

These peptides inhibit gastric secretion.

11 Claims, No Drawings

REDUCED PEPTIDES WHICH INHIBIT GASTRIC SECRETION, PROCESS FOR THEIR PREPARATION AND PHARMACEUTICAL COMPOSITIONS IN WHICH THEY ARE PRESENT

The present invention relates to new peptides which inhibit gastric secretion. It also relates to a process for their preparation and pharmaceutical compositions in which they are present.

Gastrin is a gastrointestinal hormone which is capable to a high degree of stimulating gastric secretion.

Furthermore, pentagastrin and tetragastrin are synthetic peptides similar to the terminal C sequence of the last 5 or 4 amino acids of gastrin and correspond respectively to the formulae:

Boc—beta—Ala—Trp—Met—Asp—Phe—NH$_2$ and

H—Trp—Met—Asp—Phe—NH$_2$, the alpha-amino acids and the protecting groups being designated using the 3-letter abbreviations recommended by the IUPAC-IUB Commission on Nomenclature.

These compounds also stimulate gastric secretion.

According to the present invention, it has been found, surprisingly, that peptide derivatives of these sequences become powerful inhibitors of gastric secretion by replacement of the amide link —CO—NH— between the methionine and the aspartic acid with a reduced link —CH$_2$—NH— and, if appropriate, replacement of the methionine with leucine or norleucine.

The compounds according to the invention correspond to the general formula:

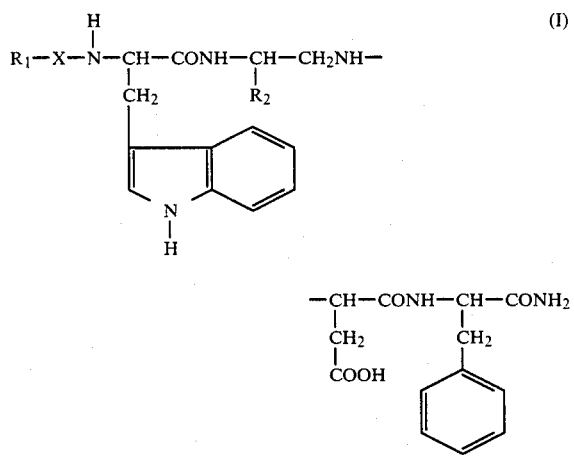

in which
R$_1$ represents hydrogen or a protecting group for the amine group, such as t-butoxycarbonyl, benzyloxycarbonyl or lower alkanoyl;
X represents beta-alanine, glycine or a direct bond between R$_1$ and the amine group; and
R$_2$ represents a group chosen from:

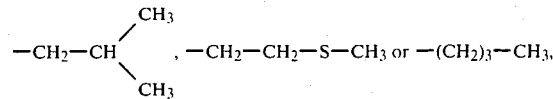

corresponding to the side chains of the natural amino acids leucine, methionine and norleucine.

The salts which the carboxyl group of the aspartic acid can form with inorganic or organic bases are an integral part of the invention.

The present invention also includes a process for the preparation of the compounds of the formula (I).

The replacement, in a peptide sequence, of an amide link with a link —CH$_2$—NH— can be achieved by reacting an appropriately substituted alpha-amino aldehyde with an alpha-amino acid in the presence of a reducing agent such as borohydride.

The reaction can be represented by the equation:

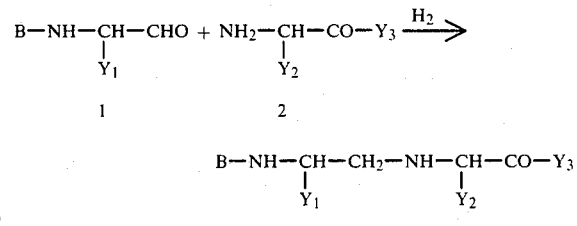

B represents a protecting group for the amine group, in particular a tert.-butoxycarbonyl group, or a peptide protected on the terminal N amine; Y$_1$ and Y$_2$ represent the side chains corresponding to the natural alpha-amino acids leucine, norleucine, methionine and aspartic acid; and Y$_3$ represents OH or the residue of phenylalaninamide.

The intermediate imine is reduced as it is formed by reaction with the hydride used, preferably sodium cyanoborohydride. The reaction is carried out in a suitable solvent, most frequently an alcohol, and at a temperature of between 20° and 50° C.

If the starting materials contain, in their side chains, substitutions capable of reacting with the aldehyde or the borohydride, they should be blocked before reaction.

Thus, the carboxyl groups will be blocked in the form of an ester, preferably the benzyl ester.

If B is a protecting group and/or Y$_3$ is OH, the reduced peptide can then be lengthened by the methods usually employed in peptide chemistry.

The aldehyde compounds 1 are themselves prepared from the corresponding alpha-amino acids. However, these compounds are chiral compounds and the optical isomerism of the starting material should be preserved in the aldehyde. This can be done using the method described in French Pat. No. 2,531,078.

This method can be represented by the equation:

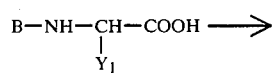

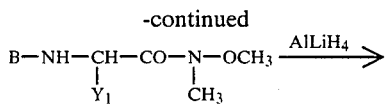

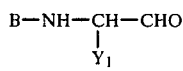

Reaction of N,O-dimethylhydroxylamine with the acid 4 gives the N,O-dimethylhydroxamate 5. Reduction of this with lithium aluminum hydride gives the aldehyde 1, which preserves the stereochemistry of the acid 4.

The fragments of the compounds (I), which are peptide fragments, can be prepared by the methods usually employed in liquid-phase peptide synthesis. Starting from the terminal C amino acid, the amino acids present in the sequence are introduced in succession.

The coupling reactions are carried out either with an activated ester of the amino acid to be introduced, in dimethylformamide and in the presence of diisopropylethylamine and 1-hydroxybenzotriazole, or with the amino acid in dimethylformamide and in the presence of benzotriazolyloxytris(dimethylamino)phosphonium hexafluorophosphate and diisopropylethylamine.

All the amino acids are incorporated in the form of the derivative protected on the amine in the alpha-position, the chosen protecting group being the t-butoxycarbonyl group. If the amino acid used has reactive groups in its side chain, these must be blocked beforehand. Thus, the acid groups in the beta-position of the aspartic acid must be blocked in the form of an ester, in particular the benzyl ester.

After each coupling reaction, deprotection of the amine in the alpha-position is effected by acid hydrolysis.

Finally, the products, protected on the groups in their side chains, are deprotected to give the compounds of the formula (I).

The examples which follow will provide a better understanding of the invention.

The following abbreviations will be used in these examples:

| Amino acids and protecting groups: | |
|---|---|
| Gly | glycine |
| Phe | L-phenylalanine |
| Asp | L-aspartic acid |
| Leu | L-leucine |
| Met | L-methionine |
| Nle | L-norleucine |
| OBzl | benzyl ester |
| Boc | t-butoxycarbonyl |
| Trp | Tryptophan. |
| ONp | 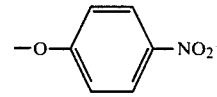 |
| OBut | tert.-butyl ester |
| OSu | N—hydroxysuccinimide ester |
| Other abbreviations: | |
| TFA | trifluoroacetic acid |
| DMF | dimethylformamide |
| DIEA | diisopropylethylamine |
| BOP | 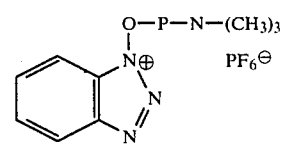 |
| HOBt | 1-hydroxybenzotriazole |

EXAMPLE 1

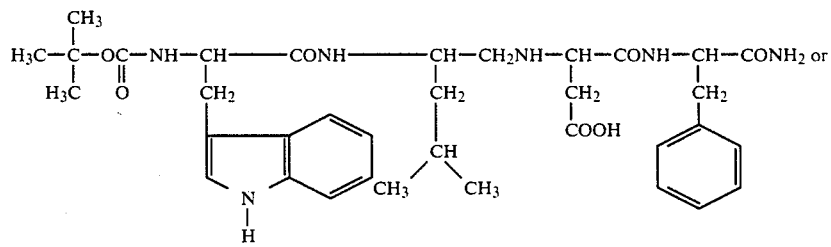

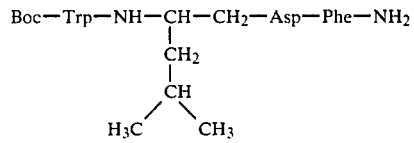

(A)

Boc—Asp(beta—OBzl)—Phe—NH₂

2.88 g of phenylalaninamide, 6.63 g of BOP and 4.85 g of Boc—Asp(beta—OBzl) are dissolved in 20 ml of DMF. 3 ml of DIEA are added and the mixture is left for 10 hours at room temperature, with stirring. The DMF is evaporated off in vacuo at a temperature below 40° C. The residue is dissolved in 250 ml of ethyl acetate and the solution is washed twice with 50 ml of a 10% solution of citric acid and once with 100 ml of water. It is dried over sodium sulfate and concentrated in vacuo.

The residue crystallizes on trituration with ether. Melting point=86°-89° C.; $[\alpha]_D = 22.5°$ (c=1.1, DMF); yield 6.5 g, i.e. 92%.

(B)

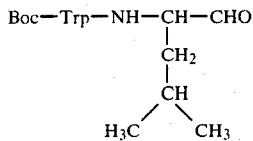

(1)

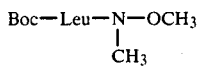

4.98 g of Boc—Leu monohydrate, 8.84 g of BOP and 2.1 g of N,O-dimethylhydroxylamine hydrochloride are dissolved in 150 ml of methylene chloride. 6.9 ml of DIEA are added and the mixture is left for 5 hours at room temperature. The solvent is evaporated off in vacuo and the residue is taken up in ethyl acetate. The solution is washed twice with a saturated solution of sodium bicarbonate, twice with a 10% solution of citric acid and once with water. The solution is dried over sodium sulfate and evaporated in vacuo.

The residue is chromatographed on a column of silica gel. Elution with an ethyl acetate/hexane mixture 1/1 vol/vol gives a colorless oil (4.5 g). Yield 82%.

Thin layer chromatography:

Rf=0.6 (ethyl acetate/hexane 1/1 vol/vol).

(2)

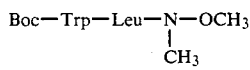

2.74 g of the product prepared above are treated with 10 ml of TFA for 30 minutes at room temperature. The TFA is evaporated off several times in vacuo in the presence of ether. The colorless oily residue is dried in a desiccator over potassium hydroxide.

The trifluoroacetate thus obtained is dissolved in 20 ml of DMF with 4.06 g of Boc—Trp—ONp, 1.4 g of HOBt and 3.75 ml of DIEA. The mixture is stirred for 10 hours at room temperature and the solvent is then evaporated off in vacuo at a temperature below 40° C. The residue is dissolved in ethyl acetate and the solution is successively washed twice with a saturated solution of sodium bicarbonate, twice with a 10% solution of citric acid and once with water. It is dried over sodium sulfate and concentrated in vacuo. The residue is chromatographed on a column of silica gel. Elution with an ethyl acetate/hexane mixture 1/1 vol/vol gives a colorless powder (3.5 g). Melting point=75°-80° C. (decomposition); yield 85%.

(3)

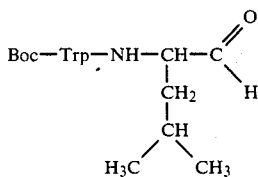

or Boc—Trp—leucinal 2.30 g of the product obtained above are dissolved in 10 ml of anhydrous tetrahydrofuran, and 50 ml of anhydrous ether are then added. 0.76 g of lithium aluminum hydride is then added in portions. After the addition has ended, the reaction is left to proceed for 45 minutes and the reaction mixture is then poured slowly into 150 ml of a cooled 10% solution of citric acid. The resulting mixture is left for 40 minutes, with stirring, and then diluted with 150 ml of ether and the organic phase is decanted. This is washed successively with a 10% solution of citric acid, water, a saturated solution of sodium bicarbonate and water. It is dried over sodium sulfate and then concentrated in vacuo at a temperature below 40° C.

A colorless oil remains which must be used quickly for the subsequent operations. However, it can be kept for a few hours in a refrigerator.

(C)

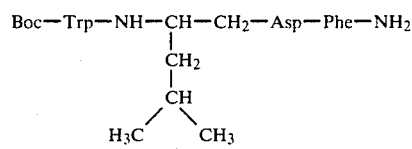

p (1)

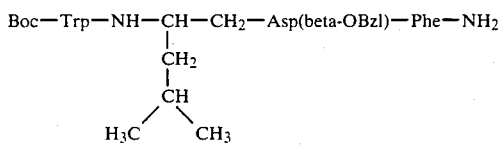

1.64 g of the protected peptide prepared in paragraph A are treated with 10 ml of TFA for 30 minutes at room temperature. 150 ml of ether are added and the precipitate which has formed is filtered off. It is washed several times with ether and then dried in vacuo.

The trifluoroacetate thus obtained is dissolved in 100 ml of methanol with the aldehyde obtained in paragraph B-3, originating from the reduction of 2.3 g of the N,O-dimethylhydroxamate.

The pH is brought to 9 by the addition of DIEA. A solution of 0.225 g of sodium cyanoborohydride in 2 ml of methanol is added and the pH is adjusted to 6 by the addition of a 10% aqueous solution of potassium bisulfate. Throughout the operation, the pH is kept between 6 and 6.5 by the addition of a 10% solution of potassium bisulfate.

After one hour, a further solution of 0.225 g of sodium cyanoborohydride in 2 ml of methanol is added and another addition (same quantity) is made after 6 hours.

The pH no longer changes after 20 hours. The mixture is concentrated in vacuo at a temperature below 40° C. The residue is taken up in ethyl acetate and the solution is washed with a saturated solution of sodium bicarbonate and then with water. It is dried over sodium sulfate and then concentrated in vacuo. The residue is chromatographed on a column of silica gel. Elution is carried out with an ethyl acetate/hexane mixture 7/3 vol/vol. Trituration of the resulting product with ether gives a colorless powder (0.43 g). Melting point=19-9°-201° C.; $[\alpha]_D = -10.5°$ (c=0.2, DMF).

According to a modified version of the process, the reaction can be carried out hot using the same quantities of reactant dissolved in 20 ml of methanol containing 0.3 ml of acetic acid. After stirring for 30 minutes, a solution of 0.65 g of sodium cyanoborohydride in 5 ml of methanol is added in portions over 35 minutes. The mixture is subsequently heated at 40° C. for 2 hours and then treated as indicated above. Chromatography on silica gel gives 0.52 g of a product identical to the one obtained previously.

(2)

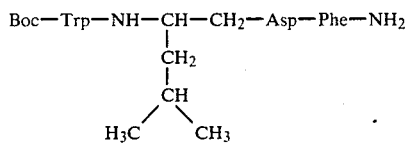

0.3 g of the compound obtained in paragraph 1 above is dissolved in 20 ml of 95° ethanol and hydrogenated, at ordinary temperature and pressure, in the presence of 0.03 g of 10% palladium-on-charcoal. After 3 hours, the catalyst is filtered off and the solvent is evaporated off in vacuo at a temperature below 40° C. The residue is triturated with ether. The solid is filtered off and washed several times with ether to give a colorless powder (0.21 g). Melting point=180° C. (decomposition); $[\alpha]_D = -20°$ (c=0.32, DMF).

EXAMPLE 2

After the addition has ended, the mixture is left for 15 minutes, with stirring, and 50 ml of ethyl acetate are added, followed by 100 ml of a cold 10% aqueous solution of citric acid. The mixture is shaken vigorously for 30 minutes and the organic phase is then separated off and washed with 50 ml of a 10% solution of citric acid and then with water. The solution is dried over magnesium sulfate and the solvent is then evaporated off in vacuo. An oil remains which is used as such in the next step.

Rf=0.86 (ethyl acetate/hexane 1/1 vol/vol).

(3)

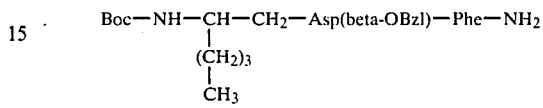

2 g of the protected dipeptide obtained in Example 1A are deprotected by reaction with 5 ml of TFA for 30 minutes. A colorless solid separates out on the addition of ether and it is filtered off, washed several times with ether and then dried in vacuo over potassium hydroxide.

This solid is dissolved in a solution of the Boc-norleucinal prepared above in 30 ml of methanol containing

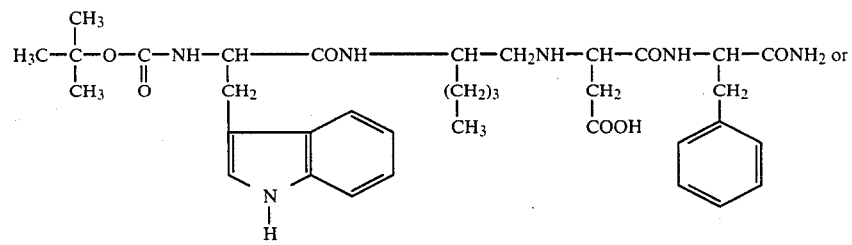

(1)

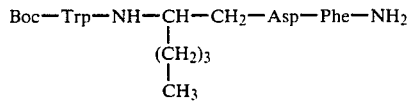

The procedure of Example 1 B-1 is followed, the leucine being replaced with norleucine. The expected product is isolated in the form of an oil.

Yield: 84%.

Rf=0.68 (ethyl acetate/hexane 1/1 vol/vol).

(2)

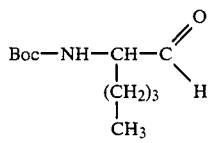

or Boc—norleucinal 0.79 g of lithium aluminum hydride is added in portions over 15 minutes to a solution, cooled to 0° C., of 1.9 g of the hydroxamate obtained above in 50 ml of ether.

1% of acetic acid.

0.8 g of sodium cyanoborohydride is then added in portions over 30 minutes at room temperature. After the addition, the mixture is left for a further 30 minutes at room temperature, the solvent is then evaporated off in vacuo and the residue is treated with 50 ml of a saturated solution of sodium bicarbonate. 3 extractions are carried out with ethyl acetate (30 ml) and the extracts are combined, washed with water and then dried over magnesium sulfate.

A solid separates out on the addition of 150 ml of hexane and it is filtered off, washed with hexane and dried in vacuo.

Weight=1.87 g.

Yield=78%.

Melting point=177°-179° C. (decomposition).

$[\alpha]_D = -14.7°$ (c=1.33, DMF).

(4)

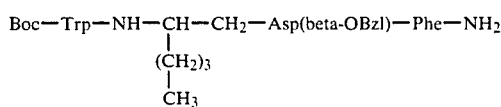

1.7 g of the above peptide are deprotected with 5 ml of TFA as indicated in paragraph 3.

The solid thus obtained is dissolved in 10 ml of DMF. 1.04 g of Boc—Trp—OSu and 1.03 ml of DIEA are added. The mixture is stirred for 3 hours at room temperature. A 5% solution of citric acid is added and the solid which has precipitated is filtered off. It is washed with water, an aqueous solution of sodium bicarbonate and water again. The solid is dried in vacuo over phosphorus pentoxide to give 1.3 g of the dry solid.

Yield=66%.

Melting point=196°–198° C. (decomposition).

$[\alpha]_D = -9.7°$ (c=1.2 DMF).

(5)

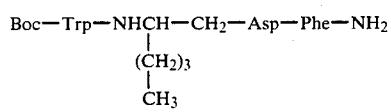

1 g of the product obtained in paragraph 4 above is subjected to catalytic hydrogenation in the presence of 10% palladium-on-charcoal by the method indicated in Example 1 C-2.

0.87 g of the expected product is isolated in the same way.

Yield 97%.

Melting point=122°–124° C. (decomposition).

$[\alpha]_D = -17.5°$ (c=0.7, DMF).

Ammonium salt

This compound is dissolved in a 0.1N solution of ammonia, the resulting solution is filtered on a millipore filter and the filtrate is lyophilized.

EXAMPLE 3

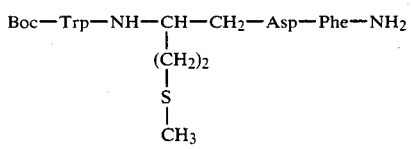

The procedure of Example 2 is followed, the L-norleucine being replaced with L-methionine. In this case, the carboxyl group on the side chain of the aspartic acid was protected in the form of the tert.-butyl ester instead of the benzyl ester. This protecting group is removed in a strong acid medium at the same time as the amino-protecting group Boc, before condensation with the tryptophan.

The following were obtained in succession:

Boc—Met—N,O—dimethylhydroxamate: Oil, Rf 0.42 (ethyl acetate/hexane 1/1 vol/vol).

Boc—methioninal: Oil, Rf 0.55 (ethyl acetate/hexane 1/1 vol/vol).

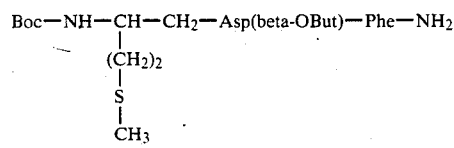

Melting point=118°–120° C. (ethyl acetate/hexane 1/1 vol/vol).

$[\alpha]_D = -7.4°$ (c=1.1, DMF).

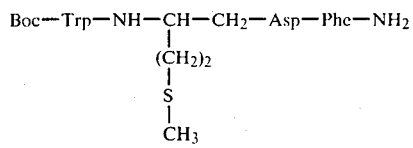

Melting point=189°–190° C. (chromatography on a silica column, eluent: ethyl acetate/pyridine/acetic acid/water 80/20/5/10 vol/vol).

$[\alpha]_D = -24.2°$ (c=1.2, DMF).

EXAMPLE 4

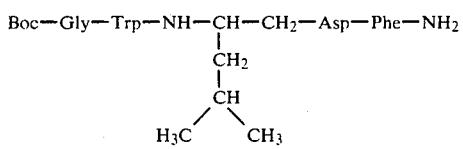

This compound was obtained from the compound of Example 1, which is deprotected by reaction with TFA as indicated above, and with which an activated ester of Boc—glycine is condensed.

Melting point=125° C. (decomposition).

$[\alpha]_D = -13.3°$ (c=0.68, DMF).

The compounds according to the invention were studied for their therapeutic properties. More particularly, these compounds were studied in vivo for their effect on gastric secretion in rats.

The model chosen for measuring the effect on secretion is reperfused anesthetized rat's stomach. The protocol adopted is a modified version of the one previously described by Ghosh and Schild.

A 300 g male rat of the Wistar strain, fasted for 18 hours, is anesthetized with urethane (10% solution, 1.5 ml/100 g, i.p.). A tracheotomy is then performed and a catheter is passed through the vein in the penis to allow the i.v. administration of the peptides. A cannula is then placed in the esophagus as far as the cardia and a second is placed in the duodenum (by means of a duodenotomy performed about 3 cm from the pylorus) as far as the gastric antral region.

A propionic/succinic acid solution (pH 5.5), which gives a linear variation in the pH as a function of the concentration of $H^+$ ions, is used to perfuse the stomach in open or closed circuit as a rate of 3 ml/minute. The body temperature and the solution temperature are monitored and kept at 30° C. The secretion of acid from the stomach causes a pH change, which is detected by a glass electrode and recorded as a function of time.

After stabilization of the basal secretion, gastrin is injected intravenously, either by perfusion or by a single injection. The response is recorded as a function of time and the quantity of acid secreted is measured on the recording chart as the difference relative to the basal secretion.

The same experiment is carried out either by i.v. injection of the peptide to be studied on the plateau of acid secretion, or by association of the peptide with the stimulant in variable concentration ratios. Finally, the peptide is administered on its own at different doses so that its agonistic effect can be examined.

The experiments carried out with the compound of Example 1 gave the following results:

AGONISTIC EFFECT

The product of Example 1 showed no agonistic effect up to a dose of 1 mg/kg.

ANTAGONISTIC EFFECT

The compound of Example 1 was studied at different doses for its antagonistic activity.

The results obtained made it possible to determine the 50% effective dose ($ED_{50}$), or the dose which causes a 50% inhibition of the gastric secretion stimulated by gastrin.

For the compound of Example 1, the $ED_{50}$ is 0.3 mg/kg.

In the same way, the compounds of Examples 2 and 3 showed no agonistic effect when studied analogously. Their antagonistic effect was apparent for a 50% effective dose of 0.3 mg/kg, respectively, for the compounds of Examples 2 and 3.

It is found from these results that:

The compounds according to the invention have practically no agonistic effect towards gastrin, despite the high value of the doses used.

The compounds according to the invention have a substantial inhibitory effect on gastric secretion under the experimental conditions used.

Furthermore, these compounds have a low toxicity.

Consequently, the compounds according to the invention may be used in human therapy in all cases where gastric secretion can usefully be reduced, and in particular for the treatment of gastroduodenal ulcers.

The compounds of the present invention are preferably administered by intravenous, intramuscular or subcutaneous injection. They are used in a solvent such as physiological serum (isotonic saline solution).

The present invention therefore also relates to the pharmaceutical compositions in which a peptide according to the invention is present as the active ingredient, in combination with a pharmaceutically acceptable vehicle such as physiological serum.

The dosage can vary according to the intensity of the desired therapeutic effect, the severity of the complaint to be treated and the method of administration used. It must therefore be determined for each patient according to these various criteria. It is most commonly between 0.1 and 10 mg of active principle per kg of body weight.

What is claimed is:

1. A peptide corresponding to the general formula:

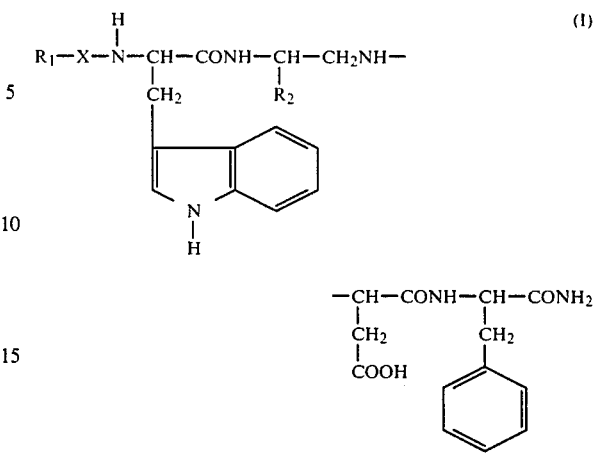

in which:
$R_1$ represents hydrogen or a protecting group for the amine group; benzyloxycarbonyl
X represents beta-alanine, glycine or a direct bond between $R_1$ and the amine group; and
$R_2$ represents a group chosen from:

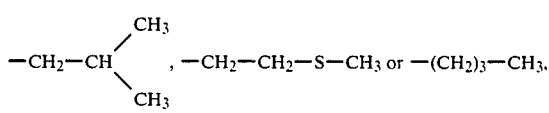

corresponding to the side chains of the natural amino acids leucine, methionine and norleucine, and also its salts with inorganic or organic bases.

2. A peptide as claimed in claim 1, which corresponds to the formula:

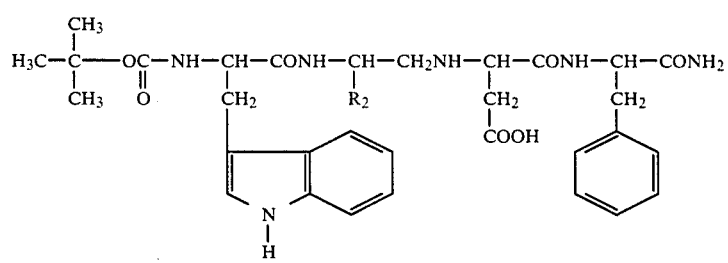

in which $R_2$ has the same meaning mentioned in claim 1.

3. A peptide as claimed in claim 1, wherein X is glycine and $R_2$ is leucine.

4. A peptide as claimed in claim 1 which is:

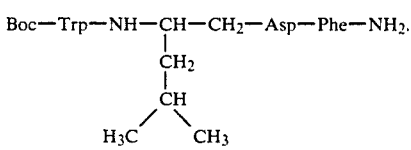

5. A peptide as claimed in claim 1 which is:

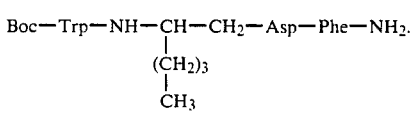

6. A peptide as claimed in claim 1 which is:

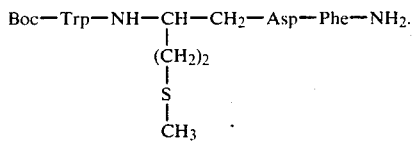

7. A peptide as claimed in claim 1 which is:

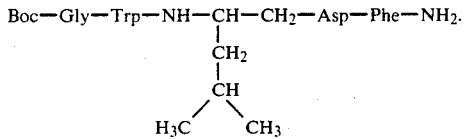

8. A peptide as claimed in claim 1 wherein $R_1$ is a protecting group which is t-butoxycarbonyl, benzyloxycarbonyl or lower alkanoyl.

9. A pharmaceutical composition for inhibiting gastric secretion which contains, as active ingredient, an effective amount for inhibiting gastric secretion of a peptide as claimed in claim 1 in association with a pharmaceutically acceptable vehicle.

10. A pharmaceutical composition for inhibiting gastric secretion which contains, as active ingredient, an effective amount for inhibiting gastric secretion of a peptide as claimed in claim 2 in association with a pharmaceutically acceptable vehicle.

11. A pharmaceutical composition for inhibiting gastric secretion which contains, as active ingredient, an effective amount for inhibiting gastric secretion of a peptide as claimed in claim 3 in association with a pharmaceutically acceptable vehicle.

* * * * *